US006999817B2

(12) United States Patent
Park et al.

(10) Patent No.: US 6,999,817 B2
(45) Date of Patent: Feb. 14, 2006

(54) CARDIAC STIMULATION DEVICE INCLUDING SLEEP APNEA PREVENTION AND TREATMENT

(75) Inventors: Euljoon Park, Stevenson Ranch, CA (US); Steve Koh, Rowland Heights, CA (US); Gene A. Bornzin, Simi Valley, CA (US)

(73) Assignee: Packsetter, Inc., Sylmar, CA (US)

( * ) Notice: Subject to any disclaimer, the term of this patent is extended or adjusted under 35 U.S.C. 154(b) by 398 days.

(21) Appl. No.: 10/077,660

(22) Filed: Feb. 14, 2002

(65) Prior Publication Data

US 2003/0153955 A1 Aug. 14, 2003

(51) Int. Cl.
*A61N 1/36* (2006.01)

(52) U.S. Cl. .............................................. 607/19; 607/9
(58) Field of Classification Search ................ 607/9, 607/17, 19, 27, 25
See application file for complete search history.

(56) References Cited

U.S. PATENT DOCUMENTS

| 4,644,954 | A | 2/1987 | Wittkampf et al. | ... 128/419 PG |
| 4,759,366 | A | 7/1988 | Callaghan | ............. 128/419 PG |
| 4,815,469 | A | 3/1989 | Cohen et al. | ................ 128/634 |
| 5,040,538 | A | 8/1991 | Mortazavi | .................... 128/633 |

(Continued)

FOREIGN PATENT DOCUMENTS

| EP | 0 940 155 A2 | 2/1999 |
| EP | 1 151 718 A2 | 4/2001 |
| EP | 1 295 623 A1 | 9/2002 |
| WO | WO 00/01438 | 1/2000 |

OTHER PUBLICATIONS

Millar, et al., "The Entrainment of Low Frequency Breathing Periodicity", CHEST/98/5, pp:1143–1148 (Nov. 1990).

Hanly, et al., "Respiraiton and Abnormal Sleep in Patients with Congestive Heart Failure", CHEST/96/3, pp: 480–488 (Sep. 1989).

Saul, et al., "Nonlinear Interactions Between Respiration and Heart Rate: Classical Physiology or Entrained Nonlinear Oscillators", IEEE, pp: 299–300 (1989).

(Continued)

*Primary Examiner*—Angela D. Sykes
*Assistant Examiner*—Roderick Bradford

(57) ABSTRACT

An implantable cardiac stimulation device comprises a physiologic sensor and one or more pulse generators. The physiologic sensor is capable of sensing a physiologic parameter. The pulse generators can generate cardiac pacing pulses with a timing based on the physiologic parameter. The timed cardiac pacing pulses can prevent a sleep apnea condition. In one example, a cardiac stimulation device has a physiologic sensor and can be configured to pace a patient's heart according to a rest mode of operation. The cardiac stimulation device uses measurements from the physiologic sensor to prevent and treat sleep apnea using a revised rest mode of operation. The revised rest mode operates under a presumption that sleep apnea is primary to a reduced heart rate, rather than secondary, so that pacing at a rate higher than the natural cardiac rate during sleep will prevent sleep apnea.

4 Claims, 8 Drawing Sheets

U.S. PATENT DOCUMENTS

| | | | |
|---|---|---|---|
| 5,113,869 A | 5/1992 | Nappholz et al. ............ 128/696 |
| 5,161,527 A | 11/1992 | Nappholz et al. ..... 128/419 PG |
| 5,184,615 A | 2/1993 | Nappholz et al. ..... 128/419 PG |
| 5,188,106 A | 2/1993 | Nappholz et al. ..... 128/419 PG |
| 5,466,254 A | 11/1995 | Helland ...................... 607/123 |
| 5,476,483 A | 12/1995 | Bornzin et al. ............... 607/17 |
| 5,485,851 A | 1/1996 | Erickson ..................... 128/716 |
| 5,549,650 A | 8/1996 | Bornzin et al. ............... 607/24 |
| 5,614,246 A | 3/1997 | Mund et al. ................ 427/2.24 |
| 5,626,622 A | 5/1997 | Cooper ......................... 607/18 |
| 5,643,327 A | 7/1997 | Dawson et al. ............... 607/24 |
| 5,778,223 A | 7/1998 | Velissaropoulos et al. .. 395/611 |
| 5,800,467 A | 9/1998 | Park et al. .................... 607/17 |
| 5,819,062 A | 10/1998 | Srikantappa ................ 395/500 |
| 5,970,494 A | 10/1999 | Velissaropoulos et al. .. 707/102 |
| 5,974,340 A | 10/1999 | Kadhiresan .................. 607/18 |
| 5,991,661 A | 11/1999 | Park et al. .................... 607/19 |
| 6,029,088 A | 2/2000 | Budgifvars et al. ........... 607/27 |
| 6,052,622 A | 4/2000 | Holmström ................... 607/28 |
| 6,058,328 A | 5/2000 | Levine et al. ................. 607/14 |
| 6,064,910 A | 5/2000 | Andersson et al. ........... 607/20 |
| 6,126,611 A * | 10/2000 | Bourgeois et al. .......... 600/529 |
| 6,128,534 A | 10/2000 | Park et al. .................... 607/17 |
| 6,132,384 A | 10/2000 | Christopherson et al. ... 600/529 |
| 6,259,948 B1 | 7/2001 | Florio et al. .................... 607/9 |
| 6,266,564 B1 | 7/2001 | Hill et al. ....................... 607/9 |
| 6,272,381 B1 | 8/2001 | Callaghan et al. ............ 607/26 |
| 6,480,733 B1 | 11/2002 | Turcott ....................... 600/516 |
| 6,574,507 B1 * | 6/2003 | Bonnet ......................... 607/20 |
| 2002/0193697 A1 | 12/2002 | Cho et al. .................... 600/529 |

OTHER PUBLICATIONS

Garrigue, et al., "Night Atrial Overdrive with DDD Pacing Results in a Significant Reduction of Sleep Apnea Episodes and QOL Improvement in Heart Failure Patients", NASPE (2001).

Balaban, et al., "Feasibility of Screening for Sleep Apnea Using Pacemaker Impedance Sensor", PACE, vol. 24, Part II, No. 313, pp: 617 (Apr. 2001).

Bornzin, et al., "Adjusting Heart Rate During Sleep Using Actvity Variance", PACE, vol. 17, Part II, pp: 1933–1938 (Nov. 1994).

Garrigue S., Bordier P., Jais P., et al. "Benefit of Atrial Pacing in Sleep Apnea Syndrome," *New England Journal of Med.*, 2002; 346: pp. 404–412.

Balaban, K., Cho Y., Mongeon L., et al. "O2 Saturation During Sleep Correlates Significantly With Pacing Lower Rate in Patients With Sleep Apnea," *PACE* 2002; 25 (Park II): p. 658, No. Abstract No. 544.

* cited by examiner

CARDIAC STIMULATION DEVICE INCLUDING SLEEP APNEA PREVENTION AND TREATMENT

CROSS-REFERENCE TO RELATED APPLICATIONS

This application is related to copending, commonly-assigned U.S. patent application Ser. No. 10/077,053, titled SLEEP APNEA THERAPY DEVICE USING DYNAMIC OVERDRIVE PACING; and U.S. patent application Ser. No. 10/077,048, tilted STIMULATION DEVICE FOR SLEEP APNEA PREVENTION, DETECTION AND TREATMENT; both applications filed Feb. 14, 2002.

FIELD OF THE INVENTION

The present invention relates to techniques for providing therapy to patients who suffer from sleep apnea.

BACKGROUND OF THE INVENTION

Sleep apnea is the cessation of breathing for a short time while sleeping. Sleep apnea has multiple classifications based on source of dysfunction. Obstructive sleep apnea results from mechanical blockage of the airway, for example due to weight of fatty neck tissue compressing the trachea. Central sleep apnea results from neurological dysfunction. Mixed sleep apnea has a combination of mechanical and neurological cause.

Upper airways of the nose and pharynx are held open during breathing by dilator muscles that counteract pressure gradients that would otherwise cause airway collapse. In obstructive sleep apnea, mechanical airway obstruction resulting from superior airway size reduction, increase in airway compliance, and reduction in airway muscle tone leads to pressure disequilibrium that tends to collapse the airways.

The nervous system controls activity of the dilator muscles and respiratory muscles, resulting in a coordinated response to stimulation or depression. Ventilatory fluctuations of hyperventilation and hypoventilation occur during sleep to facilitate breathing without conscious control, reducing the work required for breathing. Unfortunately, in obstructive sleep apnea the ventilatory fluctuations allow superior airway instability and oropharyngeal obstruction, exacerbating the difficulties and dangers of sleep apnea.

Similarly, nervous system interactions of respiratory and cardiovascular functions tend to worsen the problems that arise in sleep apnea. Cardiac arrhythmia conditions such as bradycardia, tachyarrhythmia, atrioventricular block, and ventricular extrasystole are aggravated by obstructive sleep apnea, stimulating the autonomic nervous system and further degrading respiratory performance.

Central sleep apnea is cessation of breathing due to neurological dysfunction, for example a failure to generate neuromuscular stimulation required to initiate and control a respiratory cycle. The neurological dysfunction is believed to originate in the Thalmus area of the brain and may involve primary brainstem medullary depression resulting from a tumor of the posterior fossa, poliomyletis, or idiopathic central hypoventilation. During a central sleep apnea episode, a patient may fail to breath for an extended time, for example a few seconds up to two or more minutes, then rapidly inhale, typically upon arousal from sleep.

FIG. 10 is a graph that illustrates the mechanism of sleep apnea by correlating ventilatory effort to arterial partial pressure of carbon dioxide ($PaCO_2$). Ventilatory effort is generally greater during waking conditions than while asleep. Onset of sleep results in two phenomena. First, the onset of sleep causes an increased threshold for blood carbon dioxide concentration. Second, gain or slope ($\Delta V/\Delta PaCO_2$) of the ventilatory effort increases. The increase in $PaCO_2$ threshold during sleep allows one to breathe a smaller volume of air. During sleep apnea, collapse of ventilation airways causes a decrease in arterial oxygen concentration ($PaO_2$). Arousal from sleep caused by body defense mechanisms increases upper airway muscle tone, causing the airway to open and arterial oxygen concentration to increase, thereby satisfying body oxygen requirements but setting the stage for a subsequent apnea episode.

Symptoms of sleep apnea include snoring, breath holding during sleep, rapid awakening with gasping for air, morning headaches, depression, irritability, loss of memory, lack of energy, high risk of automobile and workplace accidents, and lack of high quality sleep and resulting daytime grogginess and sleepiness.

Sleep apnea is rarely fatal but is linked to high blood pressure and increased probability of heart disease, stroke, and arrhythmias. Patients with coronary artery disease who have a blood oxygen level lowered by sleep-disordered breathing may be at risk of ventricular arrhythmia and nocturnal sudden death. Furthermore, sleep-disordered breathing may cause coronary artery disease and hypertension.

Various treatments exist for sleep apnea including medical device treatments, surgery, and drugs. The type of treatment depends on the type of sleep apnea and, for obstructive apnea, the type and location of airway obstruction and the patient's health condition. Obstructions can occur in the nose or pharynx. Obstructions in the nose may result from a deviated septum or swollen nasal passages. Obstructions in the upper pharynx may result from enlarged adenoids, long soft palate, large uvula, or large tonsils. Obstructions in the lower pharynx may result from a large or posterior-placed tongue, short jaw, or short and wide neck. Drug therapy is usually sufficient for sleep apnea treatment.

Device treatments may be separated into air pressure devices and neural stimulation devices.

The most common pressure device treatment is termed continuous positive airway pressure (CPAP) and utilizes a mask worn over the nose while sleeping. A hose connects the mask to an air pump that supplies a constant controlled air pressure to a patient's nasal passages and the trachea, preventing collapse. CPAP supplies a continuous, stable pre-determined volume of air to the nasal mask to prevent the airway passage from collapsing.

Bi-level positive airway pressure (BiPAP) treatment is related and similar to CPAP except that BiPAP allows for a reduction in airflow pressure that occurs during expiration. BiPAP allows setting of two different airway pressure levels to avoid fighting incoming air pressure in the expiration portion of the respiratory cycle.

Effectiveness of CPAP varies greatly. Some believe that CPAP is an effective treatment for sleep apnea, but is inconvenient and bothersome to use. Others believe CPAP offers little help in sleep apnea treatment. Still others relate that CPAP is harmful and actually causes sleep apnea episodes since the lung is forced into a constant elevated positive pressure. Normally the lung pressure oscillates between a negative and positive pressure.

Another problem with CPAP and BiPAP devices is the inherent inconvenience and burden of wearing a constricting mask for the sleeping hours, resulting in poor patient compliance with a treatment program.

Various neural stimulation devices are known that generate and apply electrical signals that stimulate nerves to recruit upper airway muscles and maintain muscle tone in the upper airways. Several types of sensing have been used to determine appropriate timing for delivery of muscle stimulation including monitoring of inspiratory effort, respiratory functioning, breathing through the nostrils, and electrical activity associated with contractions of the diaphragm. Problems with neural stimulation include the difficulty of ensuring stimulation of correct muscular structures in the upper airways of a particular patient since the hypoglossal nerve is nearby other structures which should not be stimulated with the structures located differently in different patients.

In addition to device treatments for sleep apnea, various surgical treatments are available. Uvulopalatopharyngoplasty (UPPP) surgery removes fleshy tissue of the uvula and tightens soft tissue of the palate and pharynx in an effort to reduce or remove tissue responsible for obstruction. Unfortunately, UPPP involves significant surgical risks including airway swelling, bleeding, considerable pain for days or weeks, and depression of breathing reflex due to application of general anesthetic, a substantial problem for sleep apnea patients with difficulty breathing while not under anesthesia. Furthermore, effectiveness rates for UPPP are low, on the order of 50% effectiveness in about 50% of patients undergoing the operation.

Laser-assisted uvulaplasty (LUAP) is a laser surgery on the uvula and soft palate that is reported to reduce snoring, but having no controlled studies that show effectiveness in reducing sleep apnea. A major problem with LUAP is that snoring is known not merely as a symptom of sleep apnea, but also as a warning sign of a sleep apnea episode. By silencing the warning provided by snoring, a patient may continue with untreated sleep apnea, which may worsen but be ignored.

Pharmaceuticals and medicines are also known treatments for sleep apnea. For example, anti-depressants such as protriptyline or depressants such as klonopin are sometimes prescribed for sleep apnea but appear to be marginally effective.

SUMMARY OF THE INVENTION

In accordance with an embodiment of the present invention, an implantable cardiac stimulation device comprises a physiologic sensor and one or more pulse generators. The physiologic sensor is capable of sensing a physiologic parameter. The device monitors to detect a resting or sleep condition and delivers a pacing therapy that prevents sleep apnea. In some embodiments, the pulse generators can generate cardiac pacing pulses with a timing based on the physiologic parameter. The timed cardiac pacing pulses can prevent a sleep apnea condition.

In another embodiment, a cardiac stimulation device has a physiologic sensor and can be configured to pace a patient's heart according to a rest mode of operation. The cardiac stimulation device uses measurements from the physiologic sensor to detect a sleeping or rest condition, and prevents sleep apnea using a revised rest mode of operation. The revised rest mode operates under a presumption that sleep apnea is primary to a reduced cardiac output during sleep, hence the increased circulation time, so that pacing at a rate higher than the natural cardiac rate during sleep will prevent or reduce sleep apnea.

The cardiac stimulation device detects a patient's sleeping state using the physiologic sensor and generates pacing pulses at a rate that is at least partly dependent on information from the physiologic sensor. The cardiac stimulation device may also detect episodes of sleep apnea using the physiologic sensor and may invoke a treatment for sleep apnea that includes pacing the heart at a rate that is at least partly dependent on information from the physiologic sensor.

In various embodiments, one or more types of sensing can be performed to detect a resting/sleep condition. One type of sensor is an activity sensor. In other examples, the cardiac stimulation device may use different physiologic sensors to prevent, manage, detect, and treat sleep apnea. Physiologic sensors that are useful to detect a sleep condition include sensors that detect characteristics of cardiac electrical polarization, and other types of sensors. For example, a physiologic sensor that measures QT interval may detect a sleep condition as a prolonged QT interval. A sensor of cardiac conductivity detects sleep as a depression in conductivity. Evoked response integral amplitude decreases during sleep while the evoked response duration increases. Cardiac contractility is reduced during sleep. Stroke volume increases when a patient is supine. A sensor of paced depolarization integral (PDI) is depressed during sleep. Blood oxygen concentration decreases in obstructive sleep apnea conditions. In some embodiments, the cardiac stimulation device is capable of detecting sleep apnea episodes based on abnormal breathing using any sensor.

One particular example of a cardiac stimulation device that detects a sleeping or rest condition, and prevents and treats sleep apnea includes a physical motion sensor as a physiologic sensor. One suitable physical motion sensor is an accelerometer. The cardiac stimulation device may derive an activity measurement and an activity variance parameter based on signals from the physical motion sensor, and detect patient state such as sleeping, waking, resting, and exercise state, patient based on the activity measurement and activity variance parameter. A large activity variance signal is indicative of an exercise state. Low activity and activity variance signals are indicative of a resting state. The cardiac stimulation device may modify rest mode operation depending on the sleeping or waking state of the patient. For prevention and treatment of sleep apnea, the device may increase the base rate while sleeping. For example, the stimulation device may increase the pacing rate over the base rate instead of lowering to the rest rate.

Various embodiments of the cardiac stimulation device use different techniques for prevention, management, detection, and treatment of sleep apnea. Other embodiments may utilize other types of physiologic sensors to detect a sleep condition. For example, a physiologic sensor that measures QT interval may detect a sleep condition since QT interval is prolonged during sleep. A sensor of cardiac conductivity may be used to detect depressed conductivity occurring during sleep. An evoked response sensor may be used to measure evoked response integral amplitude, which is decreased during sleep, evoked response duration that is increased during sleep. Various sensors of cardiac contractility may be utilized to measure contractility, which is reduced during sleep. Multiple types of sensors are capable of measuring stroke volume, which increases when a patient is supine. A sensor of paced depolarization integral (PDI) may be used to detect PDI depression during sleep. An oxygen sensor and carbon dioxide sensor measures blood oxygen concentration, which decreases in obstructive sleep apnea conditions. The cardiac stimulation device is capable of detecting sleep apnea episodes based on abnormal breathing using any sensor.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

DESCRIPTION OF THE EMBODIMENT(S)

The following describes the best mode presently contemplated for practicing the invention. The description is not to be taken in a limiting sense but is set forth to convey the general principles of operation and structure of the illustrative embodiments. The issued claims define the invention scope. In the following description, like numerals or reference designators refer to like parts or elements throughout.

Figure 1:
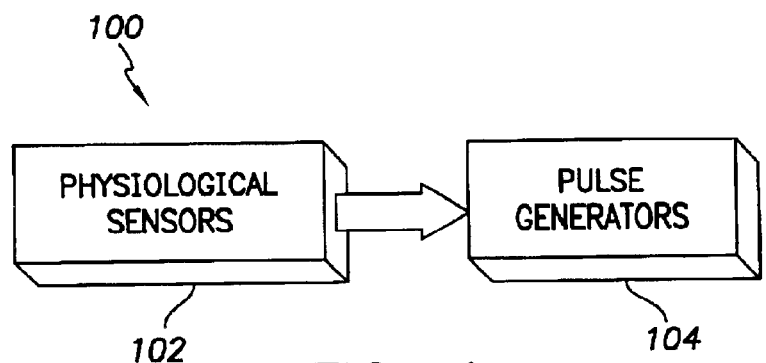
FIG. 1 is a highly schematic block diagram that depicts an example of an implantable cardiac stimulation device including one or more physiologic sensors and one or more pulse generators.

Referring to FIG. 1, a highly schematic block diagram depicts an example of an implantable cardiac stimulation device 100 that includes one or more physiologic sensors 102 and one or more pulse generators 104. The physiologic sensor 102 is capable of sensing a physiologic parameter such as activity or activity variance, respiration, minute ventilation, cardiac conductivity, blood oxygen concentration, blood carbon dioxide concentration, stroke volume, and others. Still other suitable parameters include parameters based on sensing of cardiac electrical signals, the parameters including QT interval, evoked response integral, stroke volume, paced depolarization integral (PDI), and others.

Various sensors are known to those having ordinary skill in the art that may be used to measure blood oxygen and/or blood carbon dioxide concentration. Fiber optic $PCO_2$ sensors and $PO_2$ sensors are known that are suitable for blood concentration measurements. One example is a combined Clark-type PO2/Stow-Severinghaus type PCO2 sensor for sensing both $PaO_2$ and $PaCO_2$. Other sensors include gel polymeric electrodes that contain a suitable electrolyte for measuring a selected parameter such as $PCO_2$, $PO_2$, or pH. Various other sensors may be suitable including optical fiber pH sensors, optical fiber $PCO_2$ sensors, and thermocouple temperature sensors. Suitable $PO_2$ sensors may be electrochemical $PO_2$ sensors or a fluorescent $PO_2$ sensors.

The pulse generators 104 are configured to generate cardiac pacing pulses with timing based on the physiologic parameter. The timed cardiac pacing pulses generally prevent a sleep apnea condition by pacing at a rate that is greater than the patient's intrinsic rate while sleeping. The elevated pacing rate tends to prevent the occurrence of sleep apnea.

In a more specific example, a cardiac stimulation device 100 can be configured to pace a patient's heart according to a rest mode of operation. In the rest mode, the physiologic sensor 102 may be used to determine a suitable heart rate based on the patient's level of activity at any time. When the patient is awake but not undergoing physical or psychological stress, the cardiac rate is set to a suitable average rate for the resting level of activity. The resting rate is typically set according to various calibrated parameters that can be programmed by a health care worker or can be automatically determined. When the physiologic sensor detects a higher level of physical or psychological activity, the physiologic sensor 102 detects the activity and generally sets a higher pacing rate. Conversely, when the physiologic sensor 102 detects that the patient is sleeping, pacing rate is set to a lower sleeping rate. For individual cardiac cycles, a base rate is set, typically to an exercise rate, a resting rate, and a sleeping rate, although other rates may be utilized. The heart is paced at the base rate unless the cardiac stimulation device detects an intrinsic heartbeat prior to the time a pacing pulse is to be delivered. In a suitable modified rest mode of operation, the sleeping rate is set higher than the resting rate to prevent sleep apnea. The particular rate to prevent sleep apnea may be set based on the physiologic sensor measurement.

In addition to preventing sleep apnea, the cardiac stimulation device 100 may detect episodes of sleep apnea using the physiologic sensor 102 and may invoke a treatment for sleep apnea that includes pacing the heart at a rate that is at least partly dependent on information from the physiologic sensor.

Figure 2:
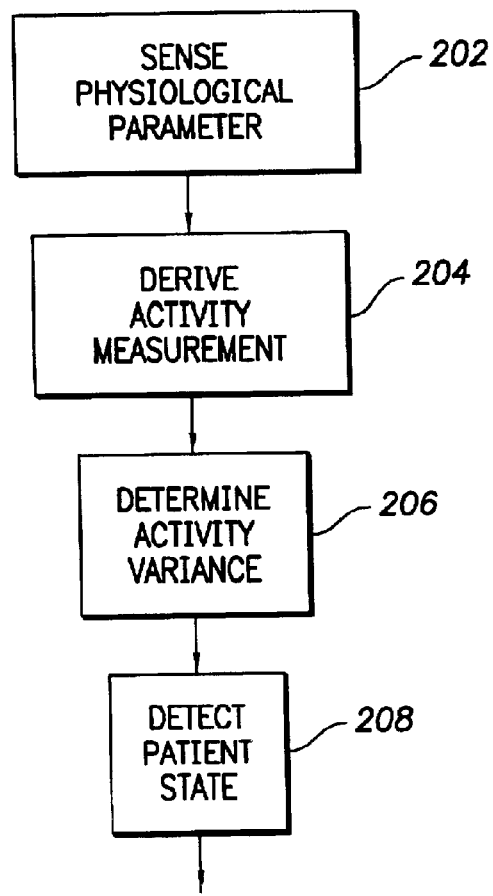
FIG. 2 is a highly schematic flow chart that illustrates an example of actions executed by the cardiac stimulation device to manage sleep apnea based on a sensed physiologic parameter.

Referring to FIG. 2, a highly schematic flow chart is depicted that illustrates an example of actions executed by the cardiac stimulation device 100 to manage sleep apnea 200 based on a sensed physiologic parameter. The flow chart describes an overview of the operation and features implemented in one embodiment of the device 310. In the flow chart, and the additional flow charts described herein, the various acts are summarized in individual actions. The actions or decisions are performed as the operation proceeds. Where a processor or equivalent element is employed, flow charts may describe operations of a control program or executable control logic that may be used by such a processor or equivalent element to effectuate desired control of the stimulation device. Those having ordinary skill in the art can readily write such a control program based on the flow charts and other descriptions presented herein.

One suitable physical motion sensor is an accelerometer. The cardiac stimulation device samples an accelerometer signal in a sense physiologic parameter action 202. Typically, the accelerometer output signal is bandpass-filtered, rectified, and integrated at regular timed intervals. The processed accelerometer signal is used as a raw activity signal. The device derives an activity measurement 204 based on the raw activity signal at intervals timed according to the cardiac cycle, then determines an activity variance parameter 206. One or both of the activity signal and the activity variance signal is used to detect patient state 208 for example from among sleeping, waking, resting, and exercise state. A large activity variance signal is indicative of a prolonged exercise state. Low activity and activity variance signals are indicative of a prolonged resting state.

The cardiac stimulation device modifies rest mode operation 210 depending on the sleeping or waking state of the patient. For prevention and treatment of sleep apnea, the device increases the base rate while sleeping. For example, the stimulation device may increase the base rate to the predetermined higher rate.

In other examples, the cardiac stimulation device may use different physiologic sensors to detect a sleep or rest condition, and prevent, manage and treat sleep apnea. Physiologic sensors that are useful to detect a sleep condition include sensors that detect characteristics of cardiac electrical polarization, and other types of sensors. For example, a physiologic sensor that measures QT interval may detect a sleep condition as a prolonged QT interval. A sensor of cardiac conductivity detects sleep as a depression in conductivity. Evoked response integral amplitude decreases during sleep while the evoked response duration increases. Cardiac contractility is reduced during sleep. Stroke volume increases when a patient is supine. A sensor of paced depolarization integral (PDI) is depressed during sleep. Blood oxygen concentration decreases in obstructive sleep apnea conditions. The cardiac stimulation device is capable of detecting sleep apnea episodes based on abnormal breathing using any sensor.

Figure 3:
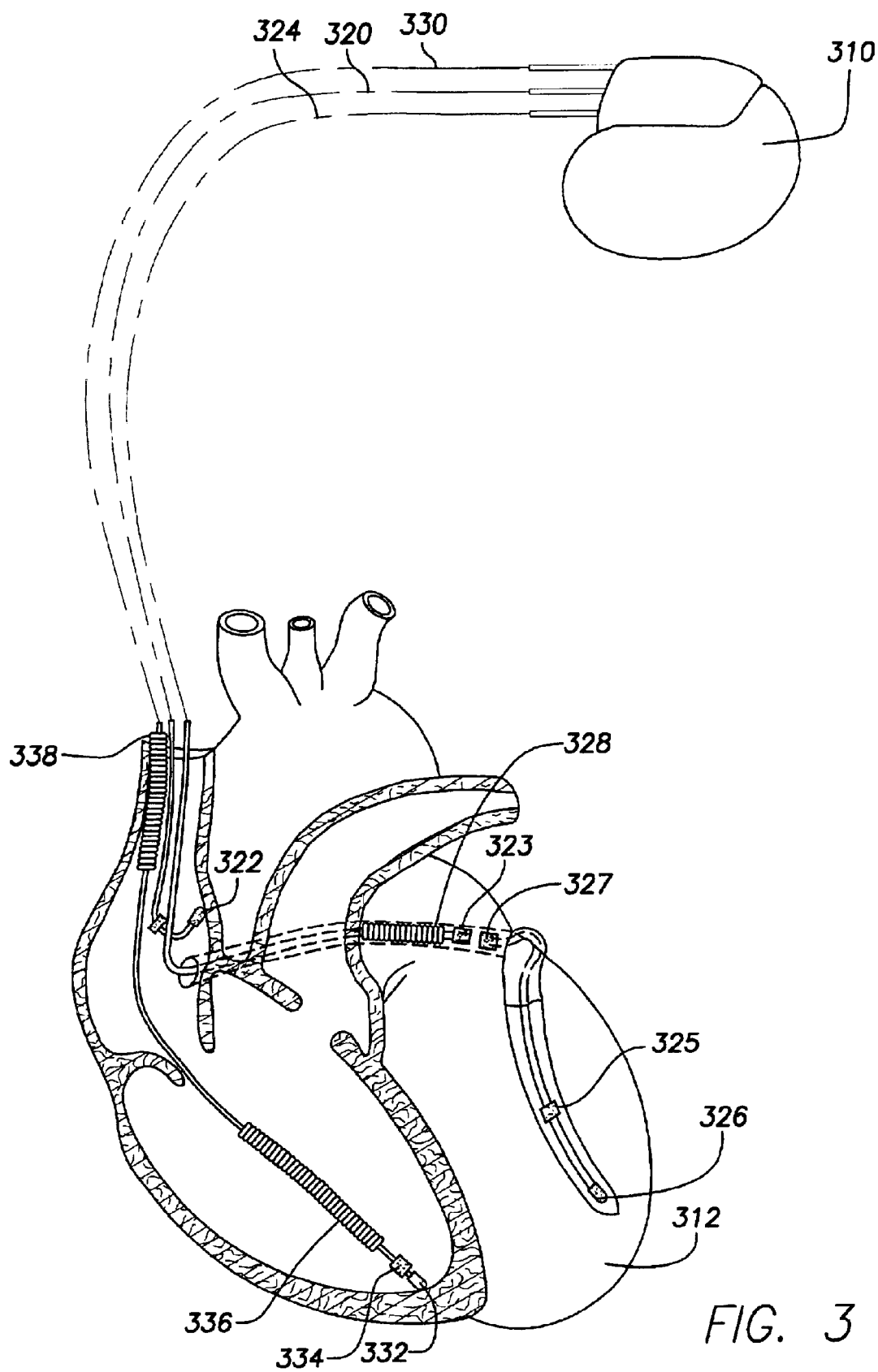
FIG. 3 is a simplified diagram illustrating an implantable stimulation device in electrical communication with at least three leads implanted into a patient's heart for delivering multi-chamber stimulation and shock therapy.

Referring to FIG. 3, a stimulation device 310 electrically couples to a patient's heart 312 using three leads 320, 324, and 330 to electrically communicate signals suitable for delivering multiple-chamber stimulation and shock therapy. The stimulation device 310 couples to an implantable right atrial lead 320 having at least an atrial tip electrode 322 to sense atrial cardiac signals and to supply right atrial chamber stimulation therapy. The atrial tip electrode 322 typically is implanted in the patient's right atrial appendage.

The stimulation device 310 is coupled to a "coronary sinus" lead 324 to sense left atrial and ventricular cardiac signals and to supply left chamber pacing therapy. The "coronary sinus" lead 324 is designed for placement in the "coronary sinus region" for positioning a distal electrode adjacent to the left ventricle and/or additional electrode(s) adjacent to the left atrium. The phrase "coronary sinus region" refers to the vasculature of the left ventricle including any portion of the coronary sinus, great cardiac vein, left marginal vein, left posterior ventricular vein, middle cardiac vein, and/or small cardiac vein or any other cardiac vein accessible by the coronary sinus.

The lead 324 may be used to supply stimulation pulses to a patient's left ventricle in biventricular pacing systems. Patients with chronic atrial fibrillation may be treated using biventricular VVIR pacemakers with left ventricular 324 and right ventricular 330 leads connected to the stimulation device 310. In patient's with spontaneous sinus rhythm, biventricular DDDR stimulating devices may be implanted with an atrial lead 320 placed in the upper right atrium and two ventricular leads 324 and 330 connected to the left and right ventricles, respectively.

An illustrative coronary sinus lead 324 is configured to receive atrial and ventricular cardiac signals and to deliver left ventricular pacing therapy using at least a left ventricular tip electrode 326. The coronary sinus lead 324 delivers left atrial pacing therapy using at least a left atrial ring electrode 327. The coronary sinus lead 324 delivers shocking therapy using at least a left atrial coil electrode 328. U.S. patent application Ser. No. 09/457,277, filed Dec. 8, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), that are hereby incorporated herein by reference, contain a complete description of a suitable coronary sinus lead.

FIG. 3 shows the stimulation device 310 electrically coupled with the patient's heart 312 by an implantable right ventricular lead 330. The right ventricular lead 330 in the illustrative embodiment has a right ventricular tip electrode 332, a right ventricular ring electrode 334, a right ventricular (RV) coil electrode 336, and an SVC coil electrode 338. Typically, the right ventricular lead 330 is transvenously inserted into the heart 312 to place the right ventricular tip electrode 332 in the right ventricular apex, positioning the RV coil electrode 336 in the right ventricle and the SVC coil electrode 338 in the superior vena cava. Inserted in this manner, the right ventricular lead 330 is capable of receiving cardiac signals and delivering stimulation in the form of pacing and shock therapy to the right ventricle.

Figure 4:
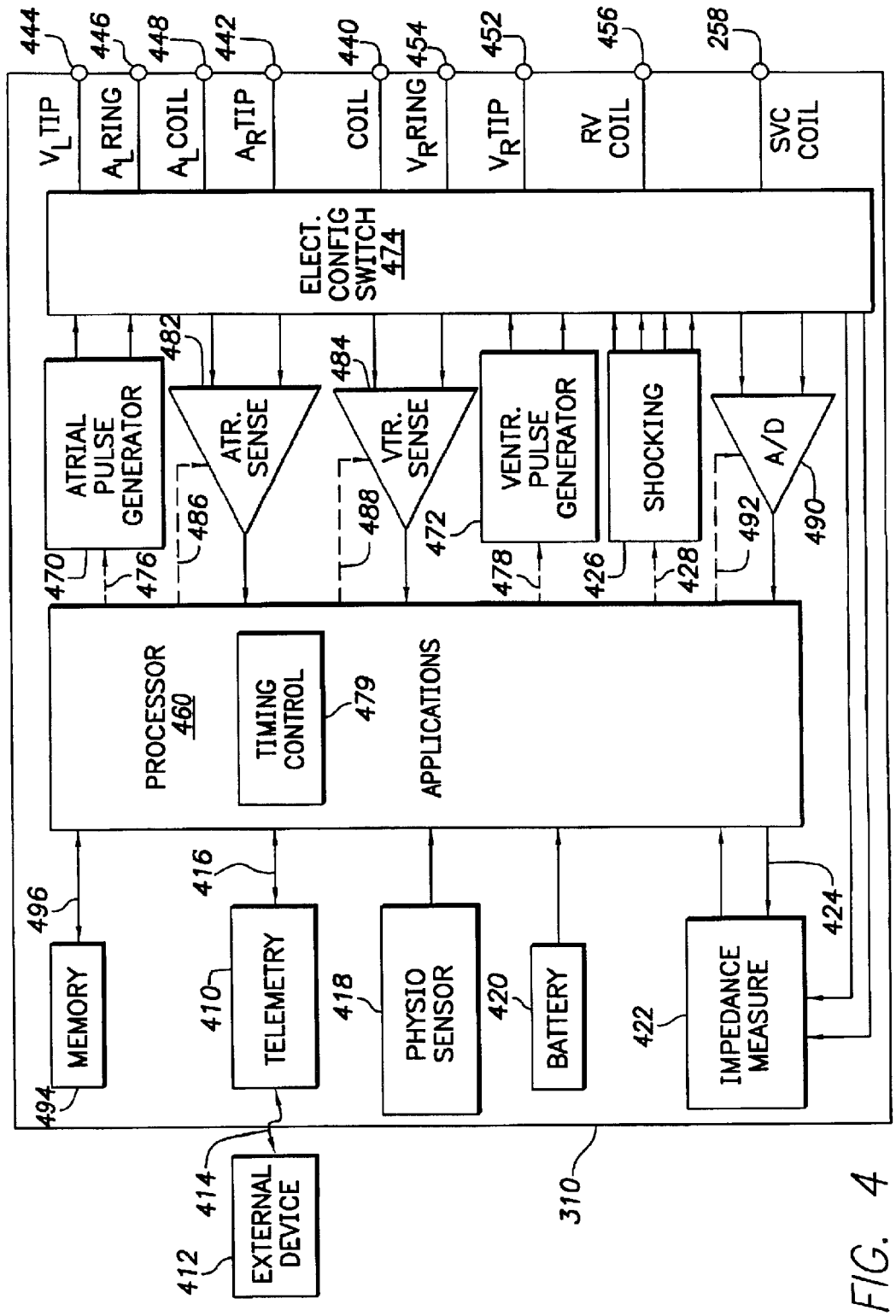
FIG. 4 is a functional block diagram that shows a multi-chamber implantable stimulation device illustrating basic elements of a stimulation device capable of cardioversion, defibrillation and pacing stimulation in four chambers of the heart.

Referring to FIG. 4, a simplified block diagram shows the multiple-chamber implantable stimulation device 310 that is capable of treating both fast and slow arrhythmias with stimulation therapy such as cardioversion, defibrillation, and pacing stimulation. The particular multi-chamber device is shown for illustration purposes only, and one of ordinary skill in the art can readily duplicate, eliminate, or disable various portions of circuitry in any desired combination to produce a device capable of delivering treatment in a desired chamber or chambers. Suitable treatments include, but are not limited to cardioversion, defibrillation and pacing stimulation, in either or both the atria and ventricles.

The housing 440 for the stimulation device 310, shown schematically in FIG. 4, is often referred to as the "can", "case" or "case electrode" and may be selected, for example by programming, to function as a return electrode for all "unipolar" modes. The housing 440 may also or otherwise be used as a return electrode alone or in combination with one or more of the coil electrodes, 328, 336 and 338, for delivering shocking stimulation to tissue. The housing 440 includes a connector (not shown) with a plurality of terminals 442, 444, 446, 448, 452, 454, 456, and 458. The terminals are shown schematically with, for convenience, names of the electrodes that are connected to the terminals shown next to the appropriate terminals. For example, at least a right atrial tip terminal ($A_R$ TIP) 442 is adapted for connection to the atrial tip electrode 322 to perform right atrial sensing and pacing.

To sense, pace, and shock in the left heart chambers, the connector includes at least a left ventricular tip terminal ($V_L$ TIP) 444, a left atrial ring terminal ($A_L$ RING) 446, and a left atrial shocking terminal ($A_L$ COIL) 448. The left ventricular tip terminal ($V_L$ TIP) 444 is adapted for connecting to the left ventricular ring electrode 325. The left atrial ring terminal ($A_L$ RING) 446 is configured to connect to the left atrial tip electrode 323. The left atrial shocking terminal ($A_L$ COIL) 448 is adapted to connect to the left atrial coil electrode 328.

The connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458 to support right chamber sensing, pacing and shocking. The right ventricular tip terminal ($V_R$ TIP) 452 is formed to connect to the right ventricular tip electrode 332. The right ventricular ring terminal ($V_R$ RING) 454 is adapted to connect to the right ventricular ring electrode 334. The right ventricular shocking terminal ($R_V$ COIL) 456 can connect to the RV coil electrode 336. The SVC shocking terminal (SVC COIL) 458 is configured to connect to the SVC coil electrode 338.

A programmable processor 460 is contained in the housing 440 and controls the various modes of stimulation therapy. The processor 460 can be implemented as any suitable control device such as a microcontroller, a controller, a microprocessor, a central processing unit, a signal processor, a digital signal processor, a state machine, a control logic, discrete control circuitry, or any similar control circuitry. In some embodiments, the processor 460 is designed specifically for controlling the delivery of stimulation therapy. The processor 460 may include RAM or ROM memory, logic and timing circuitry, state machine circuitry, and I/O circuitry. The processor 460 has a capability to process or monitor input signals or data, typically as a program code that is stored in a designated block of memory and executable by the processor 460. Details of design and operation of the processor 460 are well known to those having ordinary skill in the art so that any suitable processor 460 may be used to execute the functions described herein. Usage of microprocessor-based control circuits for performing timing and data analysis functions are well known by those having ordinary skill in the art.

Referring again to FIG. 4, an atrial pulse generator 470 and a ventricular pulse generator 472 generate pacing stimulation pulses that are delivered by the right atrial lead 320, the right ventricular lead 330, and/or the coronary sinus lead 324 via an electrode configuration switch 474. To therapeutically stimulate each of the four heart chambers, the atrial and ventricular pulse generators 470 and 472 may include dedicated, independent pulse generators, multiplexed pulse generators, or shared pulse generators. The processor 460 controls pulse generators 470 and 472 via appropriate respective control signals 476 and 478 to trigger or inhibit the stimulation pulses.

Processor 460 further includes timing control circuitry 479 to control timing of various stimulation pulse events such as pacing rate, atrio-ventricular (AV) delay, atrial interconduction (A-A) delay, or ventricular interconduction (V-V) delay, and others. The processor 460 and timing control circuitry 479 also track timing of refractory periods, blanking intervals, noise detection windows, evoked response windows, alert intervals, marker channel timing, and others. The timing control circuitry 479 times other various delays, event intervals, and timing windows that are well-known to those having ordinary skill in the art.

Switch 474 includes a plurality of switches for connecting the desired electrodes to the appropriate I/O circuits, allowing complete selective programming of electrode configuration. Typically, the processor 460 generates a control signal 480 that configures the switch 474 by selectively setting an appropriate combination of switches (not shown). In one example, the switches determine polarity of the simulation pulses from among possible unipolar, bipolar, combipolar polarities, and the like as are well known to those having ordinary skill in the art.

Atrial sensing circuits 482 and ventricular sensing circuits 484 can detect cardiac activity in each of the four heart chambers by selective coupling to the right atrial lead 320, coronary sinus lead 324, and the right ventricular lead 330, through switch 474. The atrial (ATR. SENSE) 482 and ventricular (VTR. SENSE) 484 sensing circuits typically include amplifiers of various types such as dedicated sense amplifiers, multiplexed amplifiers, or shared amplifiers. The switch 474 determines sensing polarity of the cardiac signal by selectively configuring appropriate switches in a manner that is known to those having ordinary skill in the art. Stimulation and sensing polarity control is separate so that a clinician may program sensing polarity independently from programming of stimulation polarity.

The sensing circuits 482 and 484 each generally include one or more amplifiers, bandpass filtering, and a threshold detection circuit. Suitable amplifiers are precision amplifiers with programmable gain and/or automatic gain control functionality, a feature well known to those having ordinary skill in the art. The sensing circuits 482 and 484 are programmed, either manually or automatically using a gain control algorithm to selectively sense a cardiac signal of interest. Automatic gain control enables the device 310 to effectively sense low amplitude cardiac signals, thereby managing the difficult problem of sensing low amplitude signal characteristics that occur in atrial or ventricular fibrillation conditions. Processor 460 receives output signals from atrial and ventricular sensing circuits 482 and 484. Processor 460 responds to the sensing signals by triggering or inhibiting atrial 470 and ventricular 472 pulse generators in the manner of "demand pacing" in response to the absence or presence of cardiac activity in the appropriate heart chambers. Sensing circuits 482 and 484 receive control signals from processor 460 over signal lines 486 and 488 that control gain, threshold, polarization charge removal circuitry (not shown), and timing of any blocking circuitry (not shown) that is coupled to the input terminals of the sensing circuits 482 and 484. Gain, threshold, charge removal and blocking operations are well known to those having ordinary skill in the art.

The device 310 performs arrhythmia detection utilizing the atrial and ventricular sensing circuits 482 and 484 to sense cardiac signals. In arrhythmia detection, the device 310 determines whether a rhythm is physiologic or pathologic. As used herein, the term "sensing" refers to monitoring of a cardiac signal for determining the presence of a cardiac pulse. The term "detection" refers to processing of the sensed cardiac signals to determine the presence of an arrhythmia. Processor 460 classifies cardiac signals by comparing timing intervals between sensed events to a predefined rate zone limit and analyzing other characteristics to determine an appropriate remedial therapy. Measured and monitored timing intervals between sensed events include P-waves, R-waves, and depolarization signals associated with fibrillation which are sometimes referred to as "F-waves" or "Fib-waves", such as "atrial Fib-waves" and "ventricular Fib-waves". The timing intervals are compared to a predefined rate zone limit such as bradycardia, normal, low rate VT, high rate VT, fibrillation rate zones, and other rate limits that are known to those having ordinary skill in the art. Other analytical characteristics are selected from among, but not limited to sudden onset, stability, physiologic sensors, and morphology. The device 310 delivers remedial therapies such as bradycardia pacing, anti-tachycardia pacing, cardioversion shocks or defibrillation shocks, collectively referred to as "tiered therapy".

An analog-to-digital (A/D) data acquisition system 490 also receives cardiac signals for acquisition, conversion, and storage or communication. The data acquisition system 490 is configured to acquire intracardiac electrogram signals in analog format, convert the raw analog data into a digital signal, and store the digital signals for later processing and/or telemetric transmission to an external device 412. The data acquisition system 490 couples to the right atrial lead 320, the coronary sinus lead 324, and the right ventricular lead 330 through the switch 474 to acquire cardiac signal samples across any desired pair of electrodes.

In an illustrative system, the data acquisition system 490 can operate in cooperation with the processor 460 or other detection circuitry to assist in detection of capture in response to an applied stimulus. Capture is defined as stimulation sufficient to cause the heart muscle to contract. The device 310 generates and applies an electrical stimulus to the heart with sufficient energy to depolarize the cardiac tissue, causing heart muscle contraction. The processor 460 monitors the cardiac signal during a selected time window following a stimulation pulse. Occurrence of a depolarization signal in the window indicates successful capture. The processor 460 enables capture detection by triggering the ventricular pulse generator 472 to generate a stimulation pulse, starting a capture detection window using the timing control circuitry 479 within the processor 460, and enabling the data acquisition system 490 via control signal 492. The data acquisition system 490 samples the cardiac signal during the capture detection window and, based on signal amplitude, determines whether capture has occurred.

The processor 460 is coupled to a memory 494 by a suitable data/address bus 496. Memory 494 stores programmable and/or automatically determined operating parameters used by the processor 460. Operating parameters are stored, determined, or modified, to customize the operation of the stimulation device 310 to needs of a particular patient. The operating parameters define, for example, pacing pulse amplitude, pulse duration, electrode polarity, stimulation rate, sensitivity, automatic features, arrhythmia detection criteria, and stimulation pulse characteristics. Stimulation pulse characteristics include amplitude, waveshape, and vector of each shocking pulse to be delivered to the patient's heart 312 within particular tiers of therapy. A feature of the device 310 is a capability to sense and store a relatively large amount of data, for example acquired from the data acquisition system 490. The data may then be used for subsequent analysis to guide device programming.

Operating parameters of the implantable device 310 may be non-invasively programmed into the memory 494 through a telemetry circuit 410 in telemetric communication with the external device 412, such as a programmer, transtelephonic transceiver, or a diagnostic system analyzer. The processor 460 sends a control signal 416 that activates the telemetry circuit 410. The telemetry circuit 410 communicates intracardiac electrograms and status information relating to the operation of the device 310 to the external device 412 through an established communication link 414.

In some embodiments, the stimulation device 310 can include a physiologic sensor 418, commonly called a "rate-responsive" sensor that is typically used to adjust pacing stimulation rate according to the exercise state of the patient. The physiologic sensor 418 may also be used to detect changes in cardiac output, changes in the physiologic condition of the heart, or diurnal changes in activity such as detecting sleep and wake states. The processor 460 responds by adjusting various pacing parameters such as rate, AV Delay, V-V Delay, and the like, at which atrial and ventricular pulse generators 470 and 472 generate stimulation pulses.

Although the example shows the physiologic sensor 418 included within the stimulation device 310, the physiologic sensor 418 may otherwise be located external to the stimulation device 310. An external physiologic sensor 418 may be implanted within a patient or carried by the patient. A common type of rate responsive sensor is an activity sensor such as an accelerometer or a piezoelectric crystal, mounted within the housing 440 of the stimulation device 310 that generates a measurable electrical potential when a mechanical stress resulting from physical activity is applied to the sensor. By analyzing the signal from a piezoelectric activity sensor, a rate-responsive pacemaker can detect various conditions or determine how frequently pacing pulses should be applied to the patient's heart.

Piezoelectric elements for activity sensors are commonly formed from piezoelectric crystals, such as quartz or barium titanite. More recently, activity sensors have been designed which use thin films of a piezoelectric polymer, such as polyvinylidene fluoride, rather than the more common piezoelectric crystals.

Multiple other types of physiologic sensors are suitable, including for example sensors that measure central venous blood temperature, blood oxygen content, blood pH level, QT time interval, respiration rate and/or minute ventilation, ventricular gradient, and other parameters. Generally any sensor capable of sensing a physiologic parameter that corresponds to the exercise state of the patient may be used although aspects of response time, unpredictable emotionally induced variations, side effects, and performance variability among different patients are important considerations in selection.

Some embodiments may include a "sleep state" or diurnal sensor that can detect sleep and wake states. One diurnal sensor is called an "activity variance" sensor in which an activity sensor is monitored diurnally to detect the low variance in the measurement that corresponds to the sleep state. U.S. Pat. No. 5,476,483 (Bornzin et. al), issued Dec. 19, 1995, describes a complete description of the activity variance sensor.

The stimulation device 310 includes a battery 420 that supplies operating power to all of the circuits shown in the device 310. For a stimulation device 310 that is capable of delivering a shocking therapy, a suitable battery 420 is capable of operating at low current drains for long periods of time, but also be capable of generating high-current pulses for capacitor charging when the patient requires a shock pulse. A suitable battery 420 has a predictable discharge characteristic so that elective replacement time can be detected. Most typically, the device 310 employs lithium/silver vanadium oxide batteries for most, if not all current devices.

The device 310 also has an impedance measuring circuit 422, which is enabled by a control signal 424 from the processor 460. The impedance measuring circuit 422 is useful for one or more of several functions. Impedance measuring circuit 422 is useful for measuring respiration or minute ventilation that can be applied to rate responsive pacing or other automatic control operations. The impedance measuring circuit 422 can be configured to measure thoracic impedance to determine shock thresholds. Impedance measurements can be used to detect implant time of the device 310. The impedance measuring circuit 422 can be used for many other various operations including measurements of stroke volume, detection of heart value opening, and the like. The impedance measuring circuit 422 can be coupled to the switch 474 so that any desired electrode may be used.

In some embodiments, the stimulation device 310 is configured to operate as an implantable cardioverter/defibrillator (ICD) device. An ICD device detects arrhythmia conditions and responds to the detected arrhythmia condition by automatically applying a suitable electrical shock therapy to the heart for the purpose of terminating the detected arrhythmia. The processor 460 controls a shocking circuit 426 by way of a control signal 428. The shocking circuit 426 generates shocking pulses of low (up to 0.5 Joules), moderate (0.5–10 Joules), or high energy (11 to 40 Joules), under control by the processor 460. Shocking pulses are applied to the patient's heart 312 through at least two shocking electrodes, selected from the left atrial coil electrode 328, the RV coil electrode 336, and/or the SVC coil electrode 338. The housing 440 may be used as an active electrode in combination with the RV coil electrode 336, or as part of a split electrical vector using the SVC coil electrode 338 or the left atrial coil electrode 328, for example using the RV electrode as a common electrode.

Cardioversion shock energy is a relatively low to moderate energy level to reduce pain felt by the patient. The cardioversion shock can be synchronized with an R-wave cardiac signal and can be part of tachycardia treatment. Defibrillation shock energy is generally a moderate to high energy level, for example corresponding to thresholds in the range of 5–40 Joules, and is delivered asynchronous with respect to intrinsic cardiac activity since R-waves may be insufficiently organized for synchronous stimulation utility. Defibrillation shocks are applied exclusively to treatment of fibrillation. Processor 460 is capable of controlling the synchronous or asynchronous delivery of the shocking pulses.

In a typical system, sleep apnea prevention may be implemented as a control program executed by processor 460. The control program enables stimulation device 310 to generate a pacing therapy such as a rate-responsive pacing therapy and to modulate base pacing rate. The control program may be enabled to switch the base pacing rate from a preprogrammed resting rate to a preprogrammed sleeping rate when the stimulation device 310 detects that the patient has fallen asleep. The control program also may be enabled to switch the base pacing rate from the sleeping rate to the resting rate when the stimulation device 310 determines that the patient is no longer sleeping. If the patient engages in physical activity, the control program may be enabled to cause the stimulation device 310 to increase pacing rate above the resting rate by an amount that accommodates the level of activity as measured by the sensor 418.

A start-up command received from the external programmer 412 through telemetry circuit 410 can activate the control program. The start-up command may be sent one or more times as part of an implantation procedure, and during subsequent follow-up visits.

Figure 5:
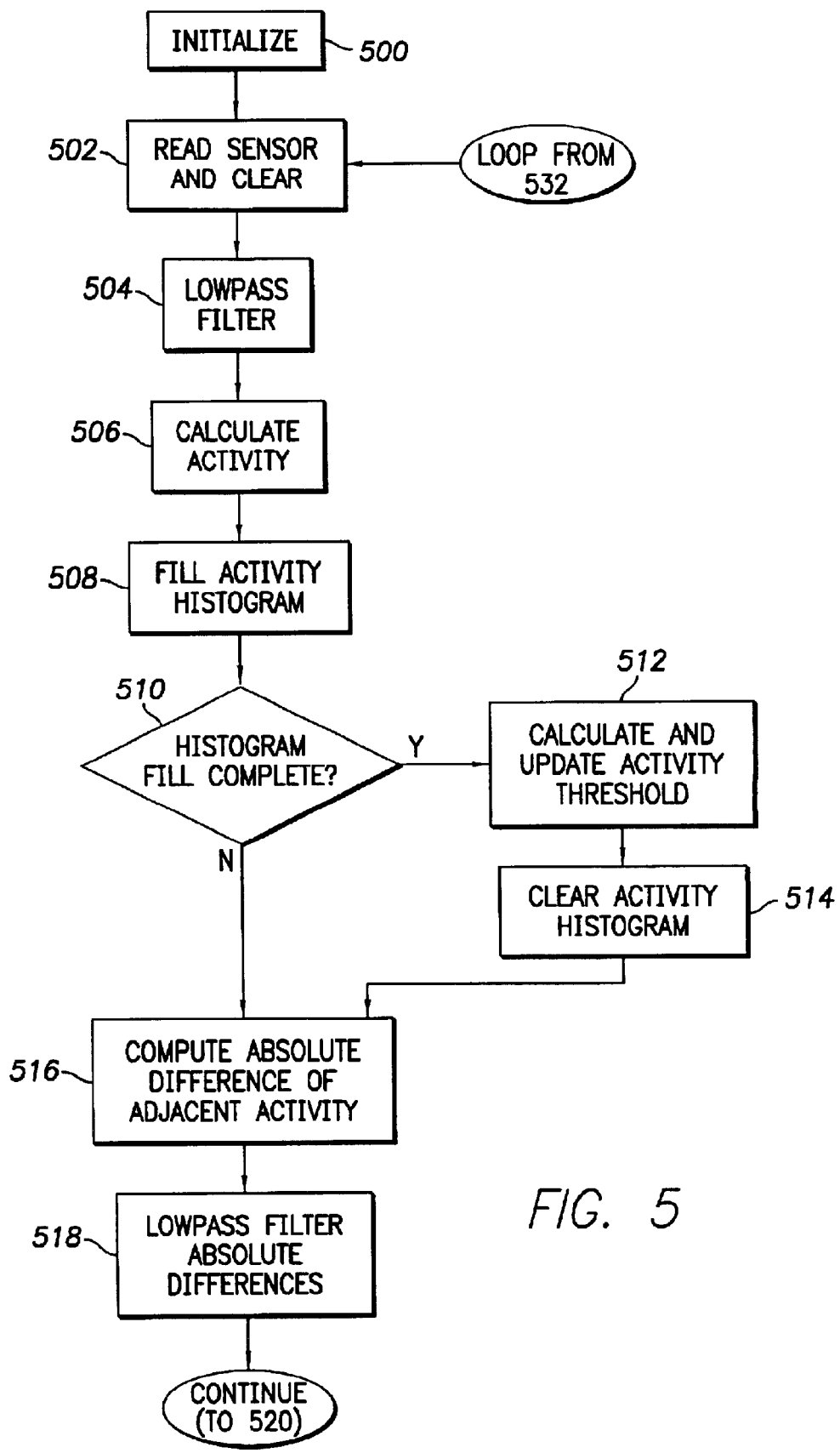
FIGS. 5 and 6 are logic flow diagrams that depict a suitable first example of a control program that modulates base pacing rate in a stimulation device.
Figure 6:
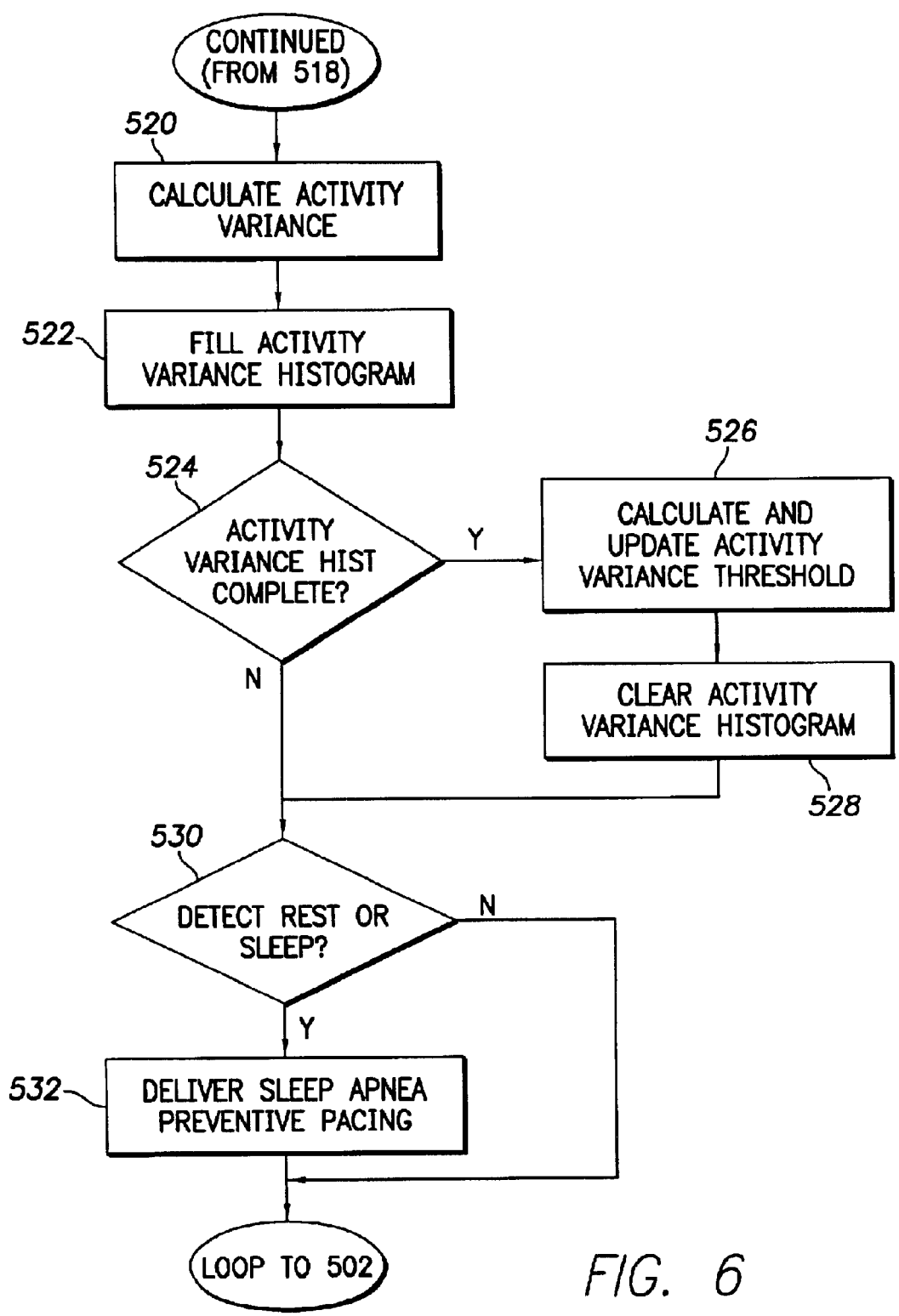

Referring to FIGS. 5 and 6 in conjunction with structures shown in FIG. 4, a logic flow diagram shows an example of a suitable control program for sleep apnea prevention. On receipt of the start-up command, processor 460 executes an initialization action 500 during which external programmer 412 sends operational parameters through the telemetry circuit 410 to the stimulation device 310 for storage in memory 494. The operational parameters include conventional pacing parameters such as pacing rate, pulse width, pulse amplitude, and the like, and special parameters that govern operation of the sensor 418. For example, a health care provider can disable base rate modulation, or entirely disable rate-responsive pacing during initialization action 500.

Parameters for implementing base rate modulation may include sleeping rate (Sleep-Rate), resting rate (Rest-Rate), sleep hours (Sleep-Hrs), activity slope (Act-Slope), and maximum pacing rate (MPR). Sleeping rate generally may be set to comfortably meet a patient's low metabolic demands during sleep, for example 55 bpm for an average patient. Resting rate is a suitable rate for an awake but inactive patient, for example 65 bpm. Sleep hours are set to the number of hours the patient typically sleeps each day, such as 7 hours. Activity slope is set to allow the stimulation device 310 to sufficiently increase or decrease pacing rate as activity level increases or decreases, for example 0.6 bpm/count. After initialization, the processor 460 adjusts activity slope according to the patient's activity profile. Maximum pacing rate is set to safely supply the patient's metabolic demands during high exertion, such as 150 bpm.

After initialization action 500, the processor 460 reads a value from a sensor in read sensor and clear action 502. Typically, processor 460 reads contents of a counter or register (not shown) associated with the sensor 418 and indicative of a sensed value, and stores the value in a variable designated Count-Val. In one example, counter contents digitally represent a patient's activity level measured during a predetermined period, for example 100 ms, within a current heartbeat interval. After reading, read-and-clear action 502 clears the counter in preparation for the next heartbeat interval.

In a lowpass filter action 504, processor 460 may average the current counter reading with one or more previous heartbeat interval counter readings. In one example shown in Equation 1, the most recent sample Count_Val and a preceding sample Count_Val_Old are averaged to avoid influence of uncharacteristically high or low measurements.

$$\text{Count\_Val}=(\text{Count\_Val}+\text{Count\_Val\_Old})/2 \quad (1)$$

In one example, variable Count_Val_Old stores the counter reading acquired during the previous heartbeat cycle, or the current counter reading immediately after initialization. Alternatively, Count_Val_Old may store a sample that is not immediately preceding or may store an average of previous samples. Some embodiments may utilize Count_Val without averaging.

In a second example of the lowpass filter action 504, processor 460 filters the value stored in Count_Val using a recursive low-pass filter to derive a digitally smoothed representation of the patient's current activity level, as shown by Equation 2:

$$\text{LastAv}=(1/16)*\text{Count\_Val}+(15/16)*\text{LastAv\_Old} \quad (2)$$

Variable LastAv stores the digitally smoothed representation of the patient's activity level. Variable LastAv_Old stores the LastAv value computed using Equation 2 during the previous cardiac cycle. At a heart rate of 72 bpm, the digital filter defined by Equation 2 has a time constant of approximately 13 seconds. During the first execution of the filter action 506, variable LastAv is effectively set to the value of Count-Val.

In a compute activity action 506, processor 460 uses the averaged sample to determine an activity value. In one example, LastAv is used to derive the patient's averaged activity level Activity by applying a recursive, low-pass digital filter to the value of LastAv according to Equation 3:

$$\text{Activity}=(1/65536)*\text{LastAv}+(65535/65536)*\text{Act\_Avg\_Old} \quad (3)$$

In the illustrative example, variable Act_Avg_Old represents the value of Act_Avg derived during the previous heartbeat cycle. At a pacing rate of 60 bpm, the time constant of the Activity digital filter is approximately 18 hours. Thus, variable Activity represents a running average of the patient's activity level, closely approximating the patient's rest activity level. During the first execution of the compute activity action 506 following initialization, the value Activity is effectively set equal to LastAv computed in filter action 504.

After determining sample, average, and activity values such as Count_Val, LastAv, and Activity, processor 460 fills an activity histogram in a fill activity histogram action 508. Generally, the fill activity histogram action 508 is a timed action so that histogram updating takes place at regular intervals. In one example, a health care provider can select the frequency of histogram updating. One suitable histogram update rate is approximately once every 26 seconds, less frequently than every heartbeat cycle to conserve space in the memory 494. The processor 460 uses the activity histogram to derive an activity threshold and, in turn, to determine whether the patient is sleeping or awake.

Figure 7:
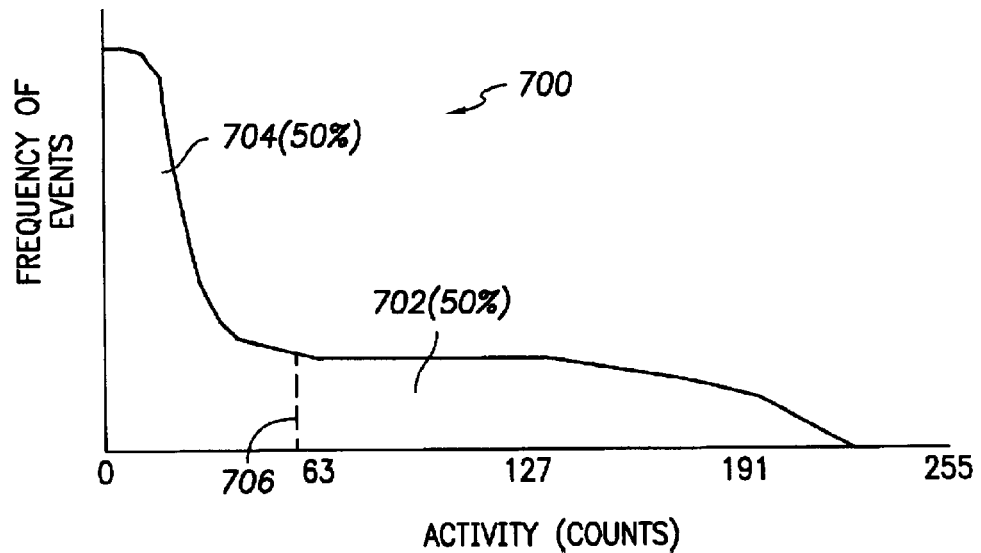
FIG. 7 is a graph that depicts an example of an activity histogram that may be filled using the fill activity histogram action.

In fill activity histogram action 508, processor 460 increments the bin of the activity histogram designated by the Activity value. The activity histogram may be maintained in the memory 494. Referring to FIG. 7, a graph depicts an example of an activity histogram 700 that may be filled using the fill activity histogram action 508. The activity histogram 700 is a distribution of the relative frequency of occurrence of activity values. In the illustrative histogram, the computed activity values can range from a minimum activity value of 0 to a maximum value of 255.

FIG. 7 shows an example of an activity histogram 700 containing data collected over a period of about one week for a typical patient. In one example, the activity histogram 700 is divided into 128 two-byte bins, each corresponding to an Activity value so that the activity histogram 700 occupies 256 bytes of memory 494.

Referring again to FIG. 5, an activity histogram fill complete logic action 510 tests to determine whether the histogram is completely filled. Histogram filling completion can be defined as the occurrence of an event such as a timing count, a completed number of samples, or external events including commands from an external programmer. The activity threshold is re-evaluated at preselected intervals, for example weekly. If the histogram fill is complete, processor 460 performs calculate and update activity threshold action 512.

In one example of a suitable calculate and update activity threshold action 512, processor 460 may estimate a Sleep_Events value that is indicative of the number of activity measurements stored in the activity histogram that were derived while the patient was sleeping. Processor 460 determines Sleep_Events according to equation 4:

$$Sleep\_Events = (Sleep\_Hrs/24) * Total\_Events \quad (4)$$

Variable Sleep_Hrs designates the number of hours the patient typically spends sleeping each day, according to programming in initialization action 500. Variable Total_Events designates the total number of activity measurements stored in the activity histogram at the time of the sleep event. A weekly histogram contains about 23,296 total events.

In one example of a technique to calculate activity threshold, processor 460 uses the Sleep_Events value to determine the activity threshold Act_Thresh. Processor 460 adds contents of all activity histogram bins starting with the lowest bin and proceeding through successively higher bins until the number of measurements corresponding to the value of Sleep-Events are counted. The final added bin is deemed to be the highest bin containing activity measurements that were derived during patient sleep. Variable Act_Thresh is set to the activity value associated with the highest added bin. In the example shown in FIG. 7, activity threshold 706 divides the activity histogram 700 into two regions including a nonactive region 704 for lower activity samples and an active region 706 for high activity samples. In the illustrative example, the nonactive region 704 and the active region 706 each contain about half the sample values.

After determining activity variance threshold, processor 460 clears the activity histogram in clear activity histogram action 514 to prepare for collection of new data over the next update period.

After clearing the activity histogram or in cases the activity histogram is not filled, processor 460 computes an activity difference value in compute absolute difference of adjacent activity action 516. The processor 460 determines the absolute difference of adjacent Activity values. A sequence of activity sample data measurements and calculated Activity values are acquired, typically with a predetermined constant time interval separating the samples. In various embodiments, the precision of the time intervals may vary. The processor 460 determines the absolute value difference between two adjacent Activity values, for example according to equation 5:

$$Diff = ABS(Last\_Av - Last\_Av\_Old) \quad (5)$$

In a lowpass filter absolute difference action 518, processor 460 computes the difference variable Diff as the absolute value of the difference between the LastAv current value of and LastAv computed at the last histogram update. In some embodiments, the processor 460 digitally smoothes the difference Diff using a recursive, low pass filter, for example according to Equation 6:

$$Act\_var = (1/32) * Diff + (31/32) * Act\_Var\_Old \quad (6)$$

Variable Act_Var stores the current smoothed difference. Variable Act_Var_Old stores the prior smoothed difference. Variable Act_Var is set to the value Diff in the first update after initialization.

Referring to FIG. 6, the flowchart continues with a calculate activity variance action 520. Processor 460 uses the filtered activity variance to determine an activity variance value. In one example, Act_var is used to derive the patient's averaged activity variance level Activity_Variance by applying a recursive, low-pass digital filter to the value of Act_var according to Equation 7:

$$Activity_{13}\ Variance = (1/65536) * Act\_var + (65535/65536) * Act\_var\_Old \quad (7)$$

In the illustrative example, variable Act_var_Old represents the value of Act_var derived during the previous heartbeat cycle. At a pacing rate of 60 bpm, the time constant of the Activity_Variance digital filter is approximately 18 hours. Thus, variable Activity_Variance represents a running average of the patient's activity level, closely approximating the patient's rest activity variance level. During the first execution of the calculate activity variance action 520 following initialization, the value Activity_Variance is effectively set equal to Act_var computed in lowpass filter absolute difference action 518.

After determining the activity variance value, processor 460 fills an activity histogram in a fill activity variance histogram action 522. Generally, the fill activity variance histogram action 522 is a timed action so that histogram updating takes place at regular intervals. A suitable histogram update rate is approximately once every 26 seconds, less frequently than every heartbeat cycle to conserve space in the memory 494. The processor 460 uses the activity variance histogram to derive an activity threshold and, in turn, to determine whether the patient is sleeping or awake.

Figure 8:
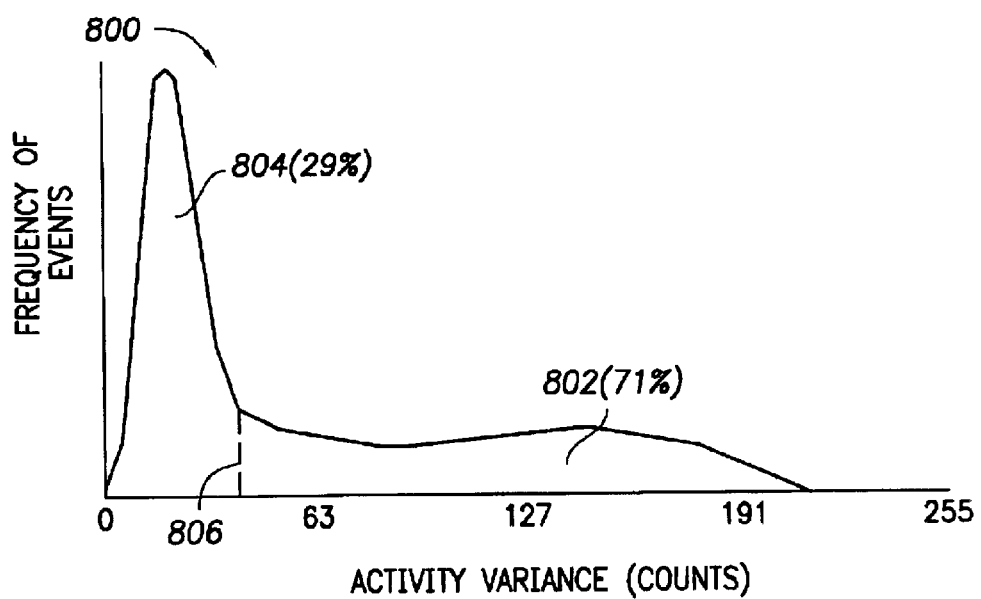
FIG. 8 is a graph that depicts an example of an activity variance histogram 800 that may be filled using the fill activity variance histogram action.

In fill activity variance histogram action 522, processor 460 increments the bin of the activity variance histogram designated by the Activity-variance value. The activity variance histogram may be maintained in the memory 494. Referring to FIG. 8, a graph depicts an example of an activity variance histogram 800 that may be filled using the fill activity variance histogram action 522. The activity variance histogram 800 is a distribution of the relative frequency of occurrence of activity variance values. In the illustrative histogram, the computed activity values can range from a minimum activity variance value of 0 to a maximum value of 255.

FIG. 8 shows an example of an activity variance histogram 800 containing data collected over a period of about one week for a typical patient. In one example, the activity variance histogram 800 is divided into 128 two-byte bins, each corresponding to an Activity_Variance value so that the activity variance histogram 800 occupies 256 bytes of memory 494.

Referring again to FIG. 6, an activity variance histogram fill complete logic action 524 tests to determine whether the histogram is completely filled. Histogram filling completion can be defined as the occurrence of an event such as a timing count, a completed number of samples, or external events including commands from an external programmer. The activity variance threshold is re-evaluated at preselected intervals, for example weekly. If the histogram fill is complete, processor 460 performs calculate and update activity variance threshold action 526.

In one example of a suitable calculate and update activity variance threshold action 526, processor 460 may estimate a Sleep_Events value that is indicative of the number of activity variance measurements stored in the activity variance histogram that were derived while the patient was sleeping. Processor 460 can determine Sleep_Events according to equation 4.

Variable Sleep_Hrs designates the number of hours the patient typically spends sleeping each day, according to programming in initialization action 500. Variable Total_Events designates the total number of activity variance measurements stored in the activity variance histogram at the time of the sleep event. A weekly histogram contains about 23,296 total events.

In one example of a technique to calculate activity threshold, processor 460 uses the Sleep_Events value to determine the activity variance threshold Act_Var_Thresh. Processor 460 adds contents of all activity variance histogram bins starting with the lowest bin and proceeding through successively higher bins until the number of measurements corresponding to the value of Sleep-Events are counted. The final added bin is deemed to be the highest bin containing activity variance measurements that were derived during patient sleep. Variable Act_Var_Thresh is set to the activity variance value associated with the highest added bin. In the example shown in FIG. 8, activity variance threshold 806 divides the activity variance histogram 800 into two regions including a nonactive region 804 for lower activity variance samples and an active region 806 for high activity variance samples. In the illustrative example, the nonactive region 804 and the active region 806 each contain about half the sample values.

The activity variance histogram 800 typically is characterized by a bimodal distribution with a higher mode 802 corresponding to activity variance measurements derived during the day while the patient is awake but relatively inactive. A lower mode 804 is a dominant mode and corresponds to activity variance measurements derived during sleep.

A bin 806 of activity variance histogram 800 is designated by the variable Act_Var_Thresh and corresponds to an activity variance measurement of about 2.5 counts. The bin 806 is estimated to be the highest bin of activity variance histogram 800 that contains activity variance measurements derived for a sleeping patient.

After determining activity variance threshold, processor 460 clears the activity variance histogram in clear activity variance histogram action 528 to prepare for collection of new data over the next update period.

After clearing the activity histogram or in cases the activity histogram is not filled, processor 460 determines whether the patient is in a resting or sleeping condition in detect rest or sleep logic action 530.

Figure 9:
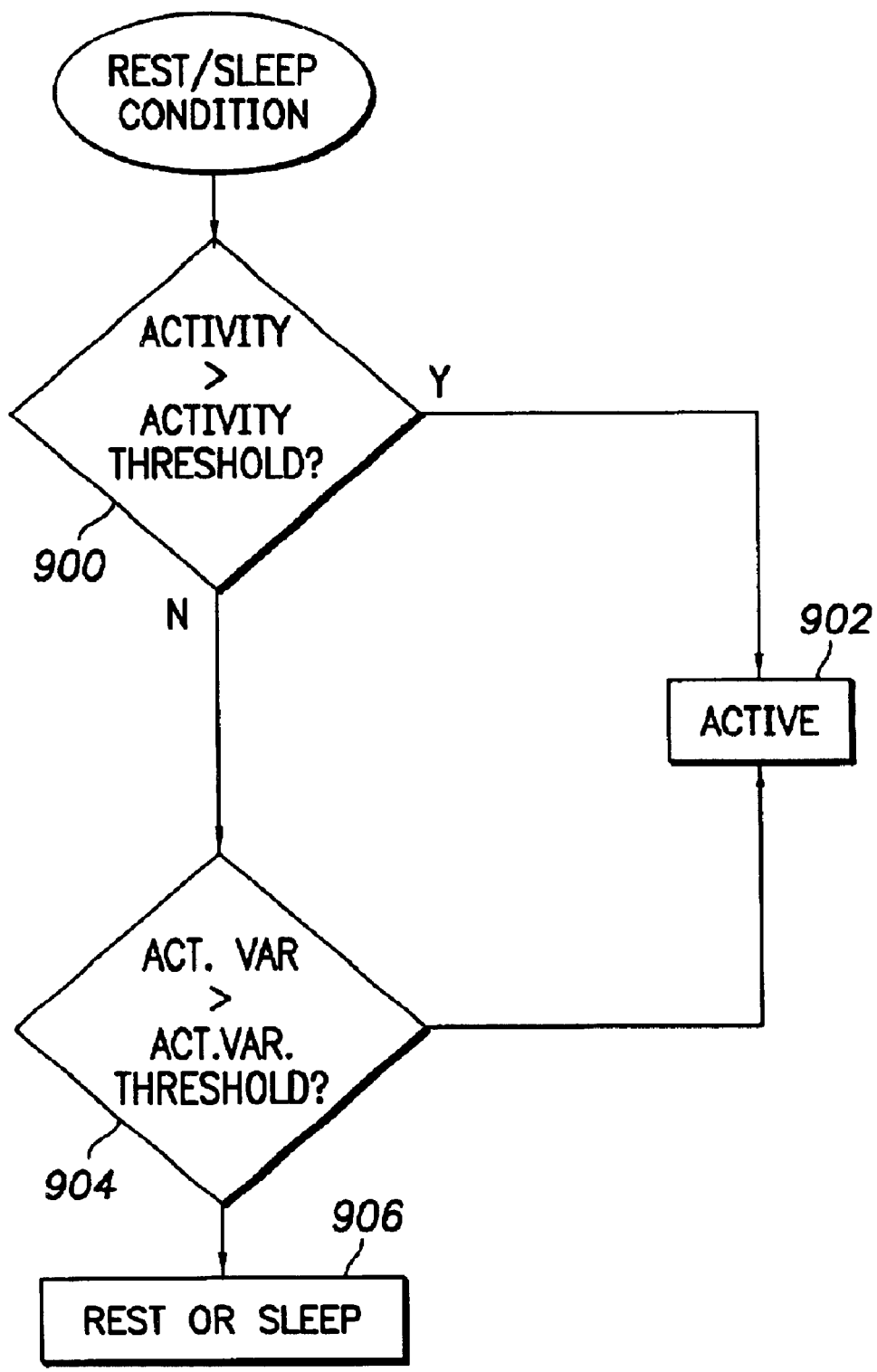
FIG. 9 is a schematic flowchart depicting an example of a suitable detect rest or sleep logic action.
Figure 10:
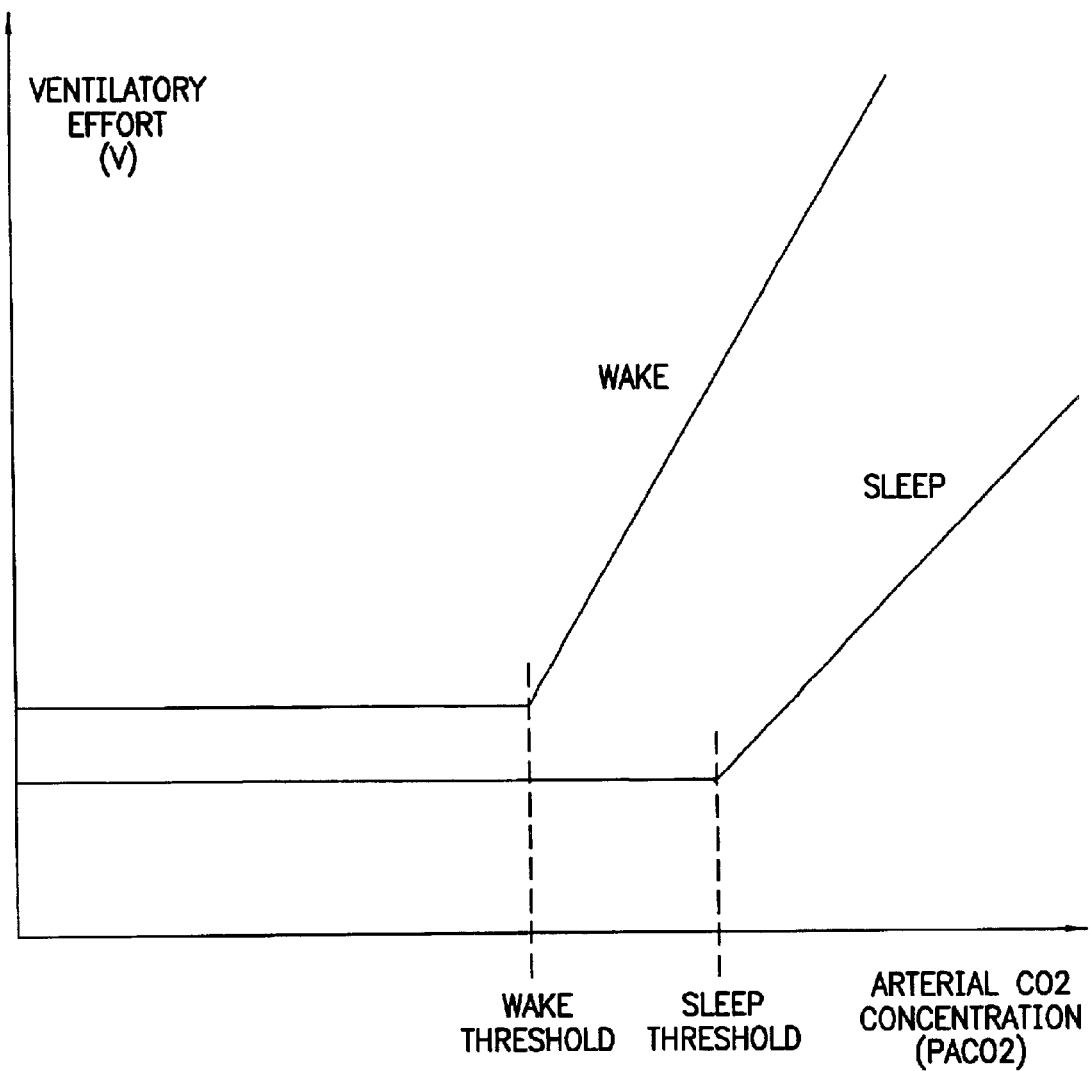
FIG. 10 is a graph that illustrates the mechanism of sleep apnea by correlating ventilatory effort to arterial partial pressure of carbon dioxide ($PaCO_2$).

Referring to FIG. 9, a schematic flow chart depicts an example of a suitable detect rest or sleep logic action 530. In a test activity logic block 900, processor 460 tests the current activity value to determine whether the current activity is greater than the activity threshold. If the current activity is greater than the activity threshold, the patient is in the active state 902. Otherwise processor 460 tests the activity variance 904 to determine whether the activity variance is greater than the activity variance threshold. If activity variance exceeds the threshold, the patient is in the active state 902. Otherwise, the patient is in a rest or sleep state 906.

Referring again to FIG. 6, if the detect rest or sleep logic action 530 determines that the state is the active state 902, then control loops back to read sensor and clear action 502 to continue activity sampling. In the rest or sleep state 906, processor 460 delivers sleep apnea preventive therapy 532. Following delivery of the preventive therapy 532 control loops back to read sensor and clear action 502 to continue activity sampling.

When the patient is sleeping and sleep apnea preventive pacing is indicated, the system may deliver a sleep apnea preventive therapy. Most generally, sleep apnea preventive pacing is cardiac pacing at a rate higher than the sleeping rate, Sleep_Rate. Various techniques can be used that prevent sleep apnea based on elevation of the cardiac rate during sleep.

In one example, processor 460 continues pacing with the pacing rate set to the Sleep_Rate value. Processor 460 can set the pacing rate to the lower Sleep_Rate level for the current heartbeat cycle by instructing the timing control circuitry 479 to lengthen the escape interval.

If another example, activity and activity variance can be monitored to determine patient state among multiple possible states including active, at rest but awake, asleep, or other levels of activity. Cardiac rate is then set according to the particular current patient state.

In another example, the processor 460 does not simply switch the base pacing rate between a sleeping rate and a resting rate but rather can use activity variance measurements to set the pacing rate to rates between a sleeping rate and a resting rate. More specifically, although the base pacing rate is bounded on the low end by a preprogrammed sleeping rate, the base pacing rate has no predetermined upper limit or resting rate. The second example does not use an activity variance histogram but rather employs a preprogrammed base rate slope applied to the activity variance measurements to determine the amount to increase the base pacing rate above the sleeping rate.

While the invention has been described with reference to various embodiments, it will be understood that these embodiments are illustrative and that the scope of the invention is not limited to them. Many variations, modifications, additions and improvements of the embodiments described are possible. For example, those of ordinary skill in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. A method of operating an implantable cardiac stimulation device consisting of:

detecting one of a resting condition or a sleep condition; and generating cardiac pacing pulses at a sleep apnea prevention rate in response to detection of one of the resting condition or the sleep condition.

2. The method of claim 1, wherein detecting one of a resting condition or a sleep condition comprises detecting a sleeping state of a patient.

3. A method according to claim 1 further comprising:

distinguishing between a sleeping condition and a waking condition of a patient;

timing generation of the cardiac pacing pulses; and controlling the timed cardiac pacing pulses at a sleep apnea prevention rate.

4. A method according to claim 1 further comprising:

distinguishing between a sleeping condition and a waking condition of a patient; and timing cardiac pacing pulse generation to pace at a rate greater than the resting rate in response to detection of a sleeping condition.

* * * * *

UNITED STATES PATENT AND TRADEMARK OFFICE
CERTIFICATE OF CORRECTION

PATENT NO. : 6,999,817 B2  Page 1 of 1
APPLICATION NO. : 10/077660
DATED : February 14, 2006
INVENTOR(S) : Euljoon Park et al.

It is certified that error appears in the above-identified patent and that said Letters Patent is hereby corrected as shown below:

On the title page at section (73), please delete "Packsetter, Inc.," and insert -- Pacesetter, Inc. --.

Signed and Sealed this

Eighteenth Day of July, 2006

JON W. DUDAS
*Director of the United States Patent and Trademark Office*